(12) United States Patent  
Davis

(10) Patent No.: US 7,549,748 B2  
(45) Date of Patent: Jun. 23, 2009

(54) FIXATION LIGHT INDICATOR FOR SLIT LAMP

(76) Inventor: Andrew Peter Davis, 14360 SE. 47th Pl., Bellevue, WA (US) 98006

( * ) Notice: Subject to any disclaimer, the term of this patent is extended or adjusted under 35 U.S.C. 154(b) by 0 days.

(21) Appl. No.: 12/109,270

(22) Filed: Apr. 24, 2008

(65) Prior Publication Data

US 2008/0198332 A1 Aug. 21, 2008

Related U.S. Application Data

(63) Continuation of application No. 11/365,572, filed on Mar. 1, 2006, now Pat. No. 7,377,644.

(60) Provisional application No. 60/748,445, filed on Dec. 8, 2005.

(51) Int. Cl.
   *A61B 3/14* (2006.01)
   *A61B 3/00* (2006.01)
   *A61B 3/10* (2006.01)
(52) U.S. Cl. .................. 351/208; 351/221; 351/200
(58) Field of Classification Search ............ 351/200, 351/205, 208, 210, 221, 245
   See application file for complete search history.

(56) References Cited

U.S. PATENT DOCUMENTS

| 5,000,563 | A | * | 3/1991 | Gisel et al. ................ 351/245 |
| 5,387,952 | A | * | 2/1995 | Byer ........................ 351/208 |
| 5,717,480 | A | | 2/1998 | Brooks et al. ............. 351/221 |
| 7,377,644 | B2 | | 5/2008 | Davis ....................... 351/208 |

* cited by examiner

*Primary Examiner*—Mohammed Hasan
(74) *Attorney, Agent, or Firm*—Black Lowe & Graham, PLLC

(57) ABSTRACT

A slit lamp includes a rest for receiving a patient's face such as the patient's forehead. The slit lamp further includes an optical portion for observing the patient's eye. A fixation light is positioned near the optical portion to direct the patient's view toward the optical portion. A sensor secures to the rest and detects proximity of the user's face to the rest. The output of the sensor controls the fixation light such that the fixation light is turned on upon detecting the positioning of the user's face at the rest. In one embodiment, a shield secures to the optical portion and first and second fixation lights secure to the shield at either side of the optical portion. First and second flanges secure to the shield proximate the fixation lights and such that each fixation light is only viewable when directly in front of the patient's eye.

21 Claims, 6 Drawing Sheets

FIXATION LIGHT INDICATOR FOR SLIT LAMP

PRIORITY CLAIM

This application is a continuation of U.S. application Ser. No. 11/365,572 filed Mar. 1, 2006, Now U.S. Pat. No. 7,377,644 B2 which claims the benefit of U.S. Provisional Application Ser. No. 60/748,445 filed Dec. 8, 2005 and entitled THE SLIT LAMP FIXATION ALARM.

FIELD OF THE INVENTION

This invention relates generally to slit lamps for observing ocular features and, more particularly to fixation lights for slit lamps.

BACKGROUND OF THE INVENTION

The slit lamp is an instrument used in eye care that provides an illuminated and magnified view of a patient's eye. The slit lamp typically includes a light projected through a slit to allow for observation of optical cross sections of the eye using an optical portion. The light is typically mounted on an articulated arm that is adjustable for observation of different portions of the eye. During examination, the patient's face is positioned against chin and forehead rests. While one eye is being examined by the optical portion, the patient is instructed to focus the other eye on a fixation light such that the examined eye is properly oriented. A small shield secures to the slit lamp and protects the examiner from coughs and sneezes, though in prior systems the shield is much too small to be effective.

In prior systems, the fixation light is a single light mounted on an arm that is attached to the portion of the slit lamp bearing the chin and forehead rests. The examiner is required to move the fixation light from one side of the slit lamp to the other when examining both eyes. When moving the optical portion from focusing on one eye to the other, the fixation light and its mounting arm tend to cause obstruction. Furthermore, since the fixation light is constantly being moved between eyes, the mechanisms enabling articulation of its mounting arm become worn, resulting in drift of the fixation light. In prior system the fixation light is positioned close to the patient's eye such that bumping of the light or its mounting arm can cause injury to the patient. The mounting arm is typically movable to a storage position to the side of the slit lamp. However, the fixation light and its mounting arm are still an obstacle to movement of the optical portion and the examiner's hand.

Further complications during examination of a patient using a slit lamp occur as the patient's face moves. It is typical for a patient to move the forehead away from the forehead rest. As a result, the examiner must "chase" the eye. As the patient moves away the eye also moves out of the range of focus of the slit lamp. As a result, the examiner typically must frequently remind the patient to stay forward against the forehead rest.

In view of the foregoing it would be an advancement in the art to provide a slit lamp facilitating the convenient non-obstructive positioning of a fixation light. It would be a further advancement in the art to provide a convenient means for maintaining a patient's forehead against a forehead rest during examination.

SUMMARY OF THE INVENTION

A slit lamp includes a rest for receiving a portion of a patient's face, such as the patient's forehead. The slit lamp further includes an optical portion for observing the patient's eye. A fixation light is positioned near the optical portion to direct the patient's line of sight toward the optical portion. A sensor, such as a touch sensor, secures to the rest and detects proximity of the user's face to the rest. The output of the sensor controls the fixation light such that the fixation light is turned on upon detecting the positioning of the user's face at the rest. When the patient moves away from the rest, the fixation light is turned off, indicating to the patient to return to the rest. In some embodiments, the sensor is coupled to a wireless transmitter configured to transmit signals corresponding to the output of the transmitter to a receiver controlling the light.

In some embodiments a shield secures to the optical portion and first and second fixation lights secure to the shield at either side of the optical portion. First and second flanges secure to the shield and extend from the shield toward the rest. The first shade positioned proximate the first fixation light between the first fixation light and the optical device and the second shade positioned proximate the second fixation light between the second fixation light and the optical device.

BRIEF DESCRIPTION OF THE DRAWINGS

Preferred and alternative embodiments of the present invention are described in detail below with reference to the following drawings.

DETAILED DESCRIPTION OF THE PREFERRED EMBODIMENT

Figure 1:
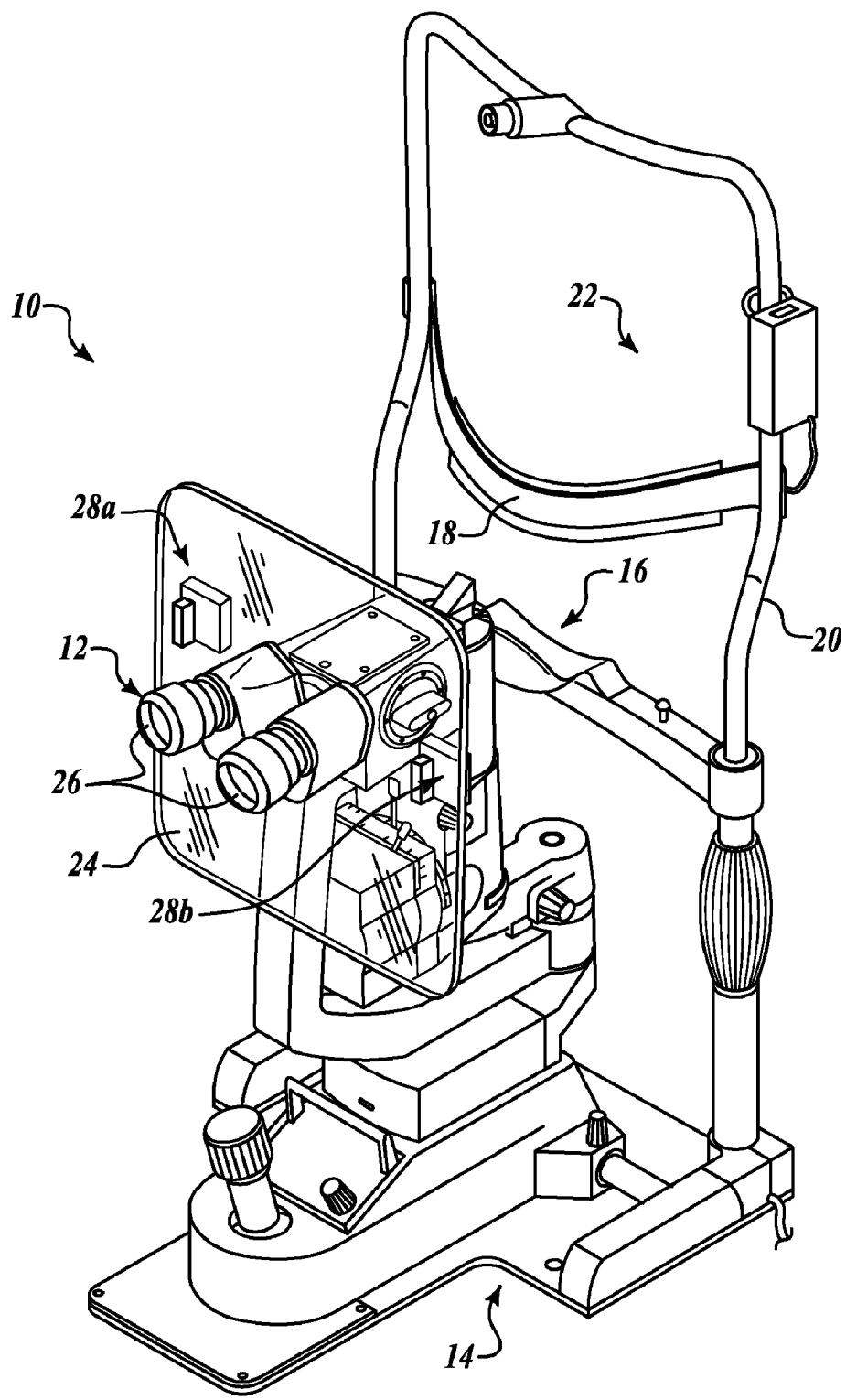
FIG. 1 is a perspective view of a slit lamp in accordance with an embodiment of the present invention.

Referring to FIG. 1, a slit lamp 10 includes an optical portion 12 housing optical structures such as magnification lenses. The optical portion 12 is mounted to a base 14 facilitating movement of the optical portion 12 relative to a patient to enable examination of both eyes and different portions of the eye. A chin rest 16 and forehead rest 18 secure to a frame 20 and receive the face of a patient during examination. In the preferred embodiment, a forehead sensor device 22 may mount to the forehead rest 18 to facilitate sensing the proximity of the forehead to the forehead rest. A shield 24 secures to the slit lamp 10 between the examiner and the patient. In the illustrated embodiment, the shield 24 secures near the eye pieces 26 of the optical portion 12.

One or more fixation lights 28a, 28b secure to the slit lamp 10 in positions to enable the lights 28a, 28b to project light into one of a patient's eyes while the other eye is being examined. In the illustrated embodiment, the fixation lights 28a, 28b secure to the shield 24 on opposite sides of the optical portion 12.

Figure 2:
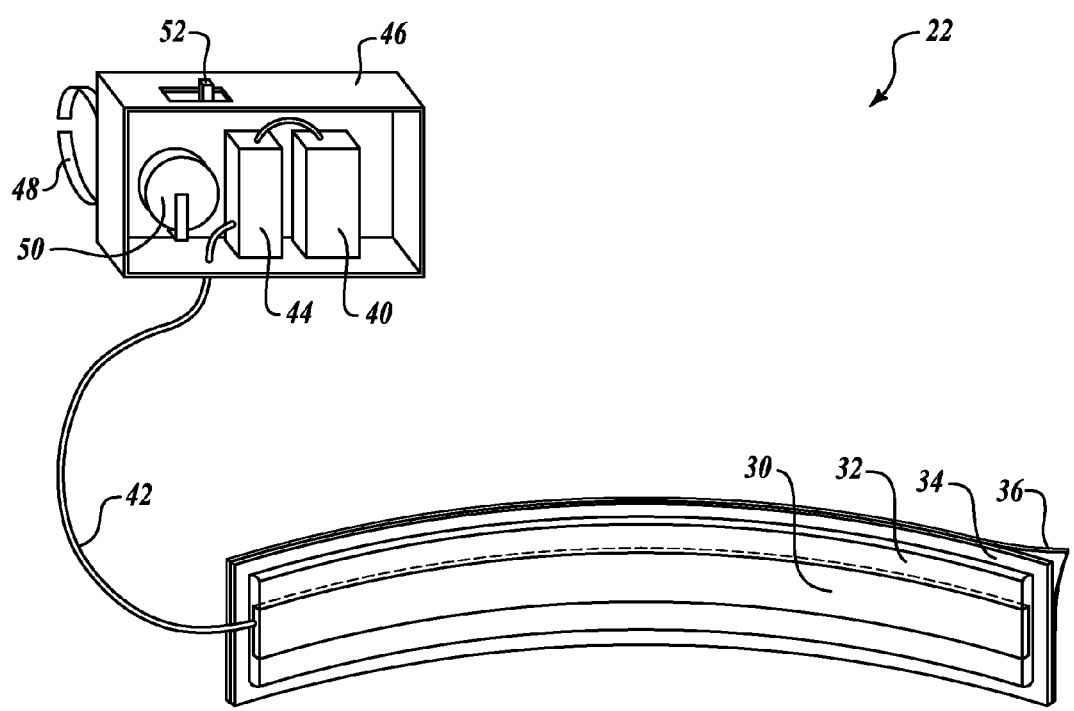
FIG. 2 is a perspective view of a sensor for use in a slit lamp forehead rest in accordance with an embodiment of the present invention.

Referring to FIG. 2, while still referring to FIG. 1, the forehead sensor device 22 includes a sensor 30 used to detect proximity of the patient's forehead to the forehead rest 18. The sensor 30 may detect proximity of the patient's forehead in a variety of ways, for example, optically, thermally, or by detecting contact of the patient's forehead with the forehead rest, e.g., via a capacitance touch sensor. The sensor 30 may include membrane switches, small mechanical switches or motion sensing switches. The sensor 30 of the forehead sensor device 22 may mount to the forehead rest 18 at the point where the forehead rest 18 secures to the frame 20 or to another portion of the slit lamp 10. For example, the sensor 30 may detect strain in the frame 20 to determine whether the patient has pressed the forehead against the forehead rest 18.

In the illustrated embodiment, the sensor 30 is a touch sensor secured within a laminate 32 or like structure that secures to the forehead rest 18. The sensor 30 may produce an output in response to the touch thereon or produce an output indicating proximity of the forehead when the pressure exerted thereon exceeds a predetermined threshold. The laminate 32 may have an adhesive backing 34 adhering the laminate 32 to the forehead rest 18. A protective layer 36 may cover the adhesive backing 34 prior to securement to the forehead rest 18.

In certain embodiments of the invention, the output of the sensor 30 controls power to the fixation lights 28a, 28b such that the lights 28a, 28b turn on when the patient's forehead is sufficiently close to the forehead rest 18. The sensor 30 may connect to the lights 28a, 28b through a wire or a wireless communication channel. In alternative embodiments, the output of the sensor 30 is used to control an audible, tactile or optical indicator or alarm that is turned on when the patient moves away from the forehead rest 18 in order to notify the patient of the need to return to the forehead rest 18. For example, a buzzer audible to the patient or a vibrating device in contact with the patient may be used. In such embodiments, the indicator may be configured to turn off when the patient returns to the forehead rest 18.

In still other embodiments, a sensor (not shown) is mounted on or near the chin rest 16 such that the fixation lights 28a, 28b are turned on only when the patient's chin is within the chin rest and the patient's forehead is against the forehead rest. In certain embodiments, separate indicators are coupled to the sensor 30 and the sensor mounted to the chin rest. For example, contact of the patient's forehead may trigger turning on of the fixation lights 28a, 28b whereas lack of contact of the patient's chin with the chin rest triggers and audible, tactile or optical alarm.

In the illustrated embodiment, the sensor 30 is electrically coupled to a transmitter 40 transmitting signals causing the fixation lights 28a, 28b to turn on or off in correspondence with proximity of the patient's forehead to the forehead rest 18. The transmitter 40 may transmit infrared, optical, radio frequency, acoustic or like signals. The output of the sensor 30 may be conducted to the transmitter 40 by means of a wire 42 coupled thereto. The output of the sensor 30 may be processed by a sensor circuit 44 and the output of the sensor circuit 44 provided to the transmitter. The sensor circuit 44 may condition the output of the sensor 30, interpret the output of the sensor to determine whether the fixation lights 28a, 28b should be turned on or off, or both condition and interpret the output. The transmitter 40 and sensor circuit 44 may mount within a housing 46 secured to the frame 20 by means of clips 48 or the like. The housing 46 may also contain a battery 50 or other power source powering the transmitter and sensor circuit 44. In an alternative embodiment, in order to conserve power life, a microprocessor (not shown) may be used to regulate power consumption. A switch 52 may secure to the housing and be used to turn off the transmitter 40 and sensor circuit when the slit lamp 10 is not in use or when the functionality of the transmitter 40 is not needed.

Figure 3:
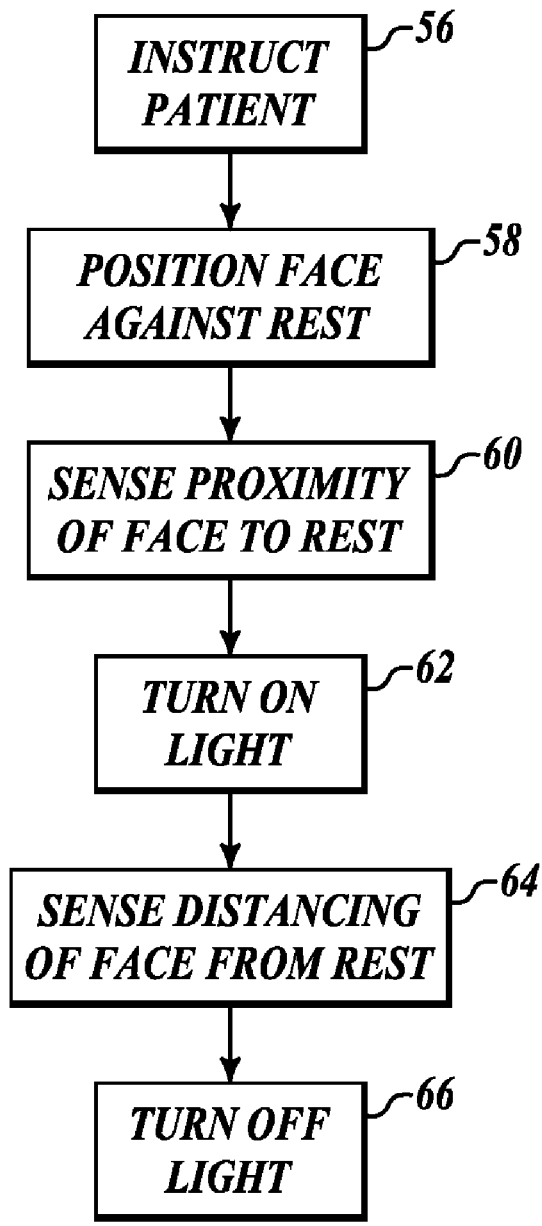
FIG. 3 is a process flow diagram of a method for using a slit lamp in accordance with an embodiment of the present invention.

FIG. 3 describes a method for using the slit lamp 10 in accordance with one embodiment of the present invention. At block 56, a patient is instructed to look at one of the fixation light 28a, 28b with the eye that is not being examined and to maintain the forehead against the forehead rest 18 such that the fixation lights 28a, 28b remains on. At block 58, the patient's face is positioned such that the patient's forehead is against the forehead rest 18 and the patient's chin is on the chin rest 16. At block 60, the proximity sensors sense the proximity of the patient's face to the forehead rest 18. If the proximity sensors determine that the patient's face is proximate, at block 62, the fixation lights 28a, 28b are illuminated. At block 64, the proximity sensors again sense the proximity of the patient's face from the forehead rest 18. If the proximity sensors determine that the patient's face is no proximate, at block 66 the fixation lights 28a, 28b are turned off.

Figure 4:
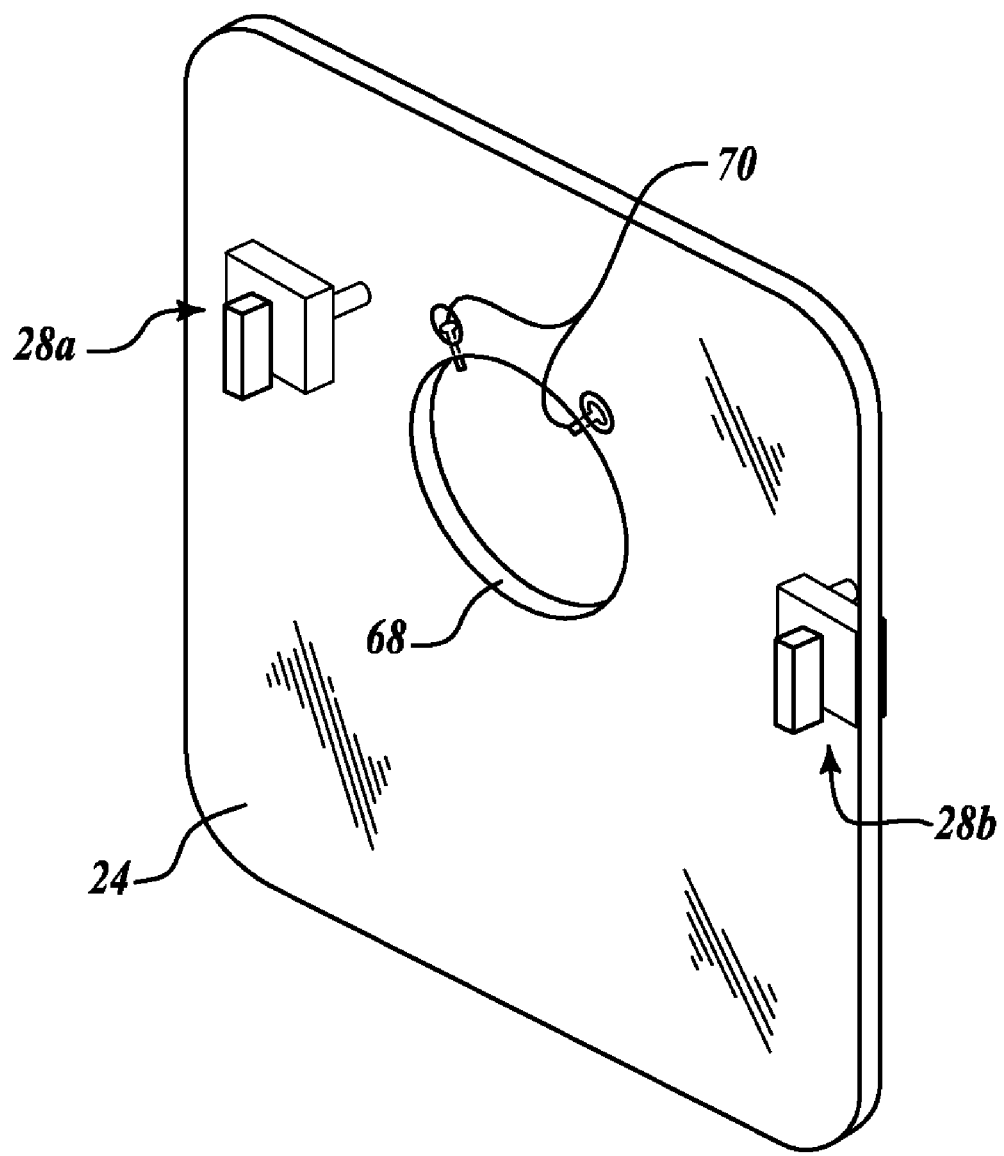
FIG. 4 is a perspective view of a shield in accordance with an embodiment of the present invention.

Referring to FIG. 4, the shield 24 may be embodied in any number of shapes such as a square or rectangular sheet and may be formed of PLEXIGLAS or like material. The shield 24 may have an aperture 68, slot 68, or like structure formed therein and sized to receive a portion of the optical portion 12 of the slit lamp 10. In the illustrated embodiment, the aperture 68 is sized to secure to the optical portion 12 behind the eye pieces 26. Fasteners 70, such as set screws or the like, secure to the shield 24 proximate the aperture and fix the position of the shield 24 relative to the optical portion 12. Fasteners 70 may also be embodied as VELCRO, adhesives, ring clamps, vise like attachments or the like. There are various types of slit lamps 12 having differently sized optical portions. Accordingly, the shield 24 may be formed of two or more pieces that are movable relative to one another and securable to one another in various configurations around the optical portion 12. Alternatively, the aperture 68 may be shaped and sized to receive most optical portions 12 and have fasteners 70 sufficiently adjustable to accommodate different optical portions 12. For example, VELCRO straps of adjustable length may be used.

Figure 5:
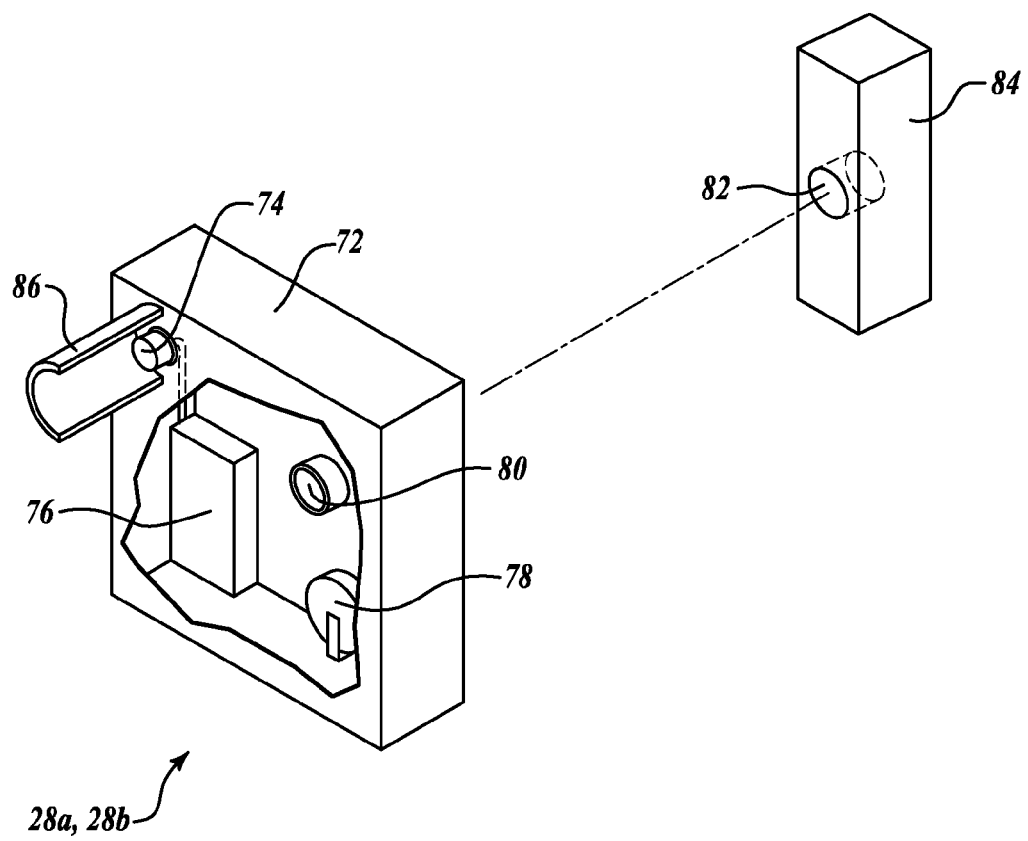
FIG. 5 is a perspective view of a fixation light in accordance with an embodiment of the present invention.

Referring to FIG. 5, while still referring to FIG. 4, the fixation lights 28a, 28b may secure to the slit lamp 10 by various means including fixed or articulated arms secured to the slit lamp 10. In the illustrated embodiment, the fixation lights 28a, 28b secure to the shield 24 on either side of the aperture 68. The fixation lights 28a, 28b may include a light housing 72 having a light source 74 such as an LED, incandescent lamp or the like. A receiver 76 is coupled to the light source 74 and to a battery 78. The receiver 76 receives signals from the transmitter 40 and permits electrical power from the battery 78 or other power source to reach the light source when the signals indicate that the patient has properly positioned the forehead against the forehead rest 18. In an alternative embodiment, in order to conserve power life, a microprocessor (not shown) may be used to regulate power consumption.

A magnet 80 secured to the housing 72 and engages an opposing magnet 82, preferably formed in a handle 84. The handle 84 is positioned opposite the shield 24 from the housing 72. In this embodiment, the attraction of the magnets 80, 82 maintains the housing and handles 84 in position. The handle 84 may be gripped by the examiner to move both the handle 84 and housing 72 in order to position the light source 74 relative to the eye of the patient.

Figure 6:
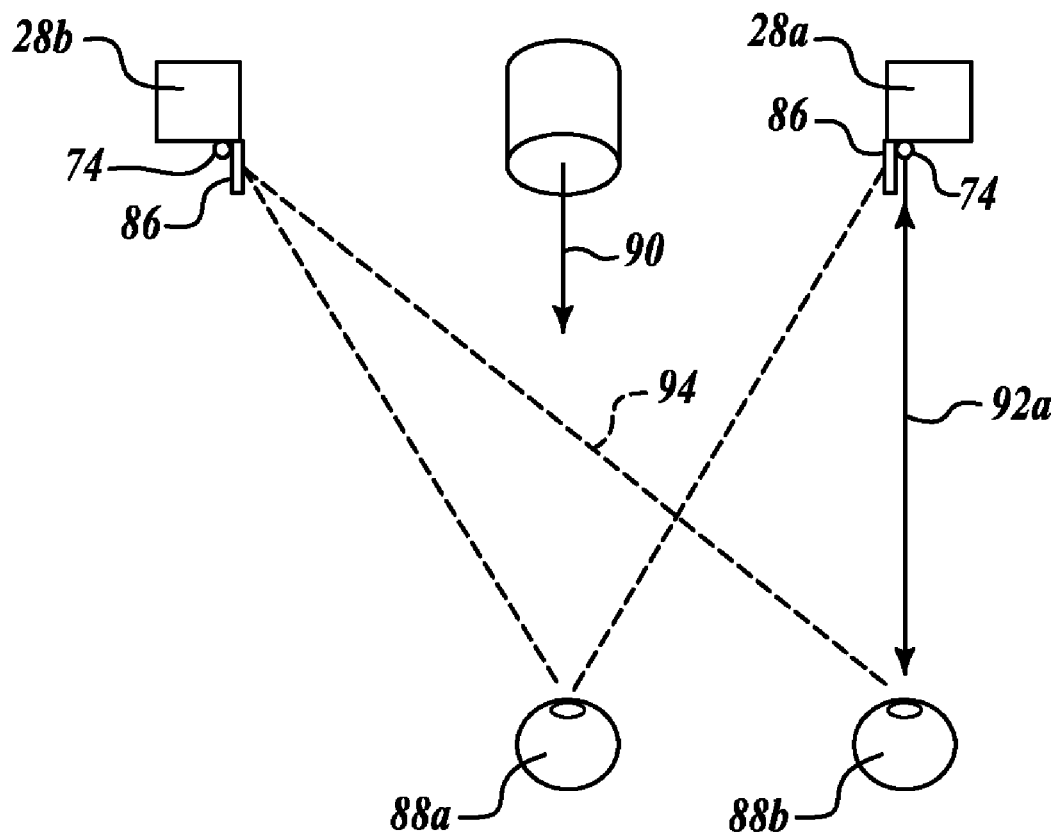
FIG. 6 is a top plan view of a slit lamp examining a patient's eyes in accordance with an embodiment of the present invention.

Referring to FIG. 6, while still referring to FIG. 5, a flange 86 extends outwardly from the housing 72 to shield the light source 74 from view from certain angles in order to avoid confusing the patient being examined. For example, the fixation light 28b may have a flange 86 positioned between its light source 74 and the optical portion 12 whereas the fixation light 28a has a flange 86 positioned between its light source 74 and the optical portion 12. In use, a patient's first eye 88a is positioned lying on the optical axis 90 of the optical portion 12 such that the eye 88a can be observed through the slit lamp. The patient's second eye 88b is positioned as illustrated such that light from the fixation light 28a is visible along the direct line of sight 92a of the second eye 88b. However, along peripheral line of sight 94, the fixation light 28b is not visible due to the flange 86 thereof. The flanges 86 of both fixation lights 28a, 28b shield the eye 88a being examined from the light sources 74. When the second eye 88b is being examined the flanges 86 likewise shield the second eye 88b from the light sources 74 while permitting the first eye 88a to observe the fixation light 28b.

Various alternative means of preventing a patient from viewing the incorrect fixation light 28a, 28b are possible. The fixation lights 28a, 28b may be positioned relative to the optical portion 12 such that the body of the optical portion 12 prevents viewing. One of the fixation lights 28a, 28b may be switched off manually or automatically by electrical or mechanical means when it is not needed. An LED with a small viewing angle may be used to prevent off-axis viewing. In an alternative embodiment, a Fresnel lens preventing off-axis viewing may be used. The fixation lights 28a, 28b may have different colors or shapes such that the patient can be instructed which light 28a, 28b to look at with the unexamined eye.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. An apparatus for observing ocular features comprising:
    an optical device;
    a rest for receiving a portion of a patient's face, the rest comprising a sensor providing an output corresponding to proximity of the patient's face to the rest;
    a transmitter coupled to the sensor, the transmitter transmitting a signal corresponding to the output of the sensor;
    a receiver coupled to the switch and configured to receive the signal;
    a light positioned to direct a line of sight of the patient toward the optical device, wherein the light is obscured to the patient's eye under examination and visible to the patient's eye not under examination; and
    a switch coupled to the light and in data communication with the sensor, the switch powering the light based on the received signal.

2. An apparatus for observing ocular features comprising:
    an optical device;
    a rest for receiving a portion of a patient's face, the rest comprising a sensor providing an output corresponding to proximity of the patient's face to the rest;
    a first light positioned to direct a line of sight of the patient toward the optical device;
    a switch coupled to the light and in data communication with the sensor, the switch powering the light based on the output of the sensor;
    a second light, whereas the optical device is positioned between the first and second lights; and
    a shield extending outwardly from the optical device, the first and second lights removably secured to the shield.

3. The apparatus of claim 2, further comprising first and second flanges secured to the shield and extending from the shield toward the rest, the first flange positioned between the first light and the optical device and the second flange positioned between the second light and the optical device.

4. The apparatus of claim 3, wherein the first and second flanges are positioned proximate the first and second lights, respectively.

5. The apparatus of claim 3, further comprising first and second housings, the first and second flanges and first and second lights securing to the first and second housings, respectively.

6. The apparatus of claim 5, wherein at least one of the first and second housings movably secure to the shield.

7. The apparatus of claim 6, further comprising:
    first and second housing magnets secured to the first and second housing; and
    first and second opposing magnets positioned proximate the first and second housing magnets, respectively, the shield positioned between the first and second housing magnets and the first and second opposing magnets.

8. An apparatus for observing ocular features comprising:
    an optical device;
    a projection extending outwardly from the optical device;
    a first light selectively securable to the projection at a plurality of positions so as to direct a line of sight of a patient toward the optical device when the patient's face is positioned proximate the optical device; and
    a second light selectively securable to the projection at a plurality of positions so as to direct a line of sight of the patient toward the optical device when the patient's face is positioned proximate the optical device.

9. The apparatus of claim 8, wherein the optical device is positioned between the first and second lights.

10. The apparatus of claim 8, wherein at least one of the first or second lights comprises a magnet capable of being selectively secured to the projection.

11. An apparatus for observing ocular features comprising:
    an optical device;
    a first light positioned proximate the optical device to direct a line of sight of a patient toward the optical device;
    a first screen positioned between the optical device and the first light to obscure the first light from a patient's eye under examination;
    a second light positioned proximate the optical device to direct the line of sight of the patient toward the optical device; and
    a second screen positioned between the optical device and the second light to obscure the second light from the patient's eye under examination.

12. The apparatus of claim 11, wherein at least one of the first and second lights is adjustably positionable proximate the optical device.

13. The apparatus of claim 11, wherein the position of at least one of the first and second screens is selectably adjustable.

14. An apparatus comprising:
- an optical device having first and second sides for observing ocular features of a patient's eye under examination;
- a first light positioned proximate the first side of the optical device
- a second light positioned proximate the second side of the optical device; and
- wherein the first light is obscured to the patient's eye under examination and visible to the patient's eye not under examination to direct a line of sight of the patient toward the optical device.

15. The apparatus of claim 14, wherein the second light is obscured to both of the patient's eyes.

16. The apparatus of claim 14, wherein at least one of the first and second lights is adjustably positionable proximate the optical device.

17. An apparatus comprising:
- an optical device having first and second sides for observing ocular features of a patient's eye under examination;
- a shield extending outwardly from the optical device;
- a first light secured to the shield proximate the first side of the optical device, wherein the first light is obscured to the patient's eye under examination and visible to the patient's eye not under examination to direct the patient's eye under examination toward the optical device; and
- a second light secured to the shield proximate the second side of the optical device.

18. The apparatus of claim 17, wherein the second light is obscured to both of the patient's eyes.

19. The apparatus of claim 17, wherein the second light is obscured to both of the patient's eyes.

20. The apparatus of claim 17, wherein the projection comprises first and second elements, wherein
- the first element extends outwardly from the first side of the optical device and the first light is secured to the first element; and
- the second element extends outwardly from the second side of the optical device and the second light is secured to the second element.

21. An apparatus comprising:
- an optical device having first and second sides for observing ocular features of a patient's eye under examination;
- a projection extending outwardly from the optical device;
- a first light secured to the projection proximate the first side of the optical device, wherein the first light is obscured to the patient's eye under examination and visible to the patient's eye not under examination to direct the patient's eye under examination toward the optical device; and
- a second light secured to the projection proximate the second side of the optical device.

* * * * *